United States Patent [19]

Vletter

[11] Patent Number: Plant 7,101

[45] Date of Patent: Jan. 9, 1990

[54] LILY PLANT NAMED GENEVE

[75] Inventor: Floris Vletter, Rijnsburg, Netherlands

[73] Assignee: Gebr. Vletter & J.A. den Haan, Netherlands

[21] Appl. No.: 261,253

[22] Filed: Oct. 24, 1988

[51] Int. Cl.[4] ..... A01H 5/00

[52] U.S. Cl. ..... Plt./68

[58] Field of Search ..... Plt./68

*Primary Examiner*—Robert E. Bagwill

*Attorney, Agent, or Firm*—Foley & Lardner, Schwartz, Jeffery, Schwaab, Mack, Blumenthal & Evans

[57] ABSTRACT

A new lily plant named Geneve characterized by its white flowers with diffuse reddish purple coloring at the edges of the base and dark purple marking.

2 Drawing Sheets

The present invention comprises a new and distinct cultivar of lily botanically known as Lilium (Asiatic hybrid), and hereinafter referred to by the cultivar name Geneve.

Geneve is a product of a planned breeding program which had the objective of creating new lily cultivars with a distinctive color.

Geneve was originated by me from a hybridization made in a controlled breeding program in Rijnsburg, The Netherlands beginning in 1980. The female parent is the cultivar known as Mont Blanc and the male parent is the cultivar named Sterling Star.

Geneve was discovered and selected by me as one flowering plant within the progeny of the stated cross in 1982 in a controlled environment in Rijnsburg, The Netherlands.

I accomplished the first act of asexual reproduction of Geneve by scaling bulbs of the initial selection in August 1982 in a controlled environment in Rijnsburg, The Netherlands. Horticultural examination of selected units initiated in 1984 has demonstrated that the combination of characteristics as herein disclosed for Geneve are firmly fixed and are retained through successive generations of asexual reproduction.

In describing the characteristics of the variety, the guidelines for the species Lilium promulgated by the International Union for the Protection of New Varieties of Plants (UPOV) have been applied. These descriptors appear in parentheses in the detailed description of the characteristics of the variety. The specific dimensions of the various parts of the plant depend on the circumstances of growing (for example, light intensity).

Geneve has not been observed under all possible environmental conditions. The phenotype may vary significantly with variations in environment such as temperature, light intensity, and day length. The following observations, measurements, and comparisons describe plants grown in Wageningen, The Netherlands under greenhouse conditions which approximate those generally used in commercial practice.

The following traits have been repeatedly observed and are determined to be basic characteristics of Geneve which in combination distinguish this lily as a new and distinct cultivar.

1. The distinctive flower color of Geneve.
2. Flower structure which includes branching at an angle of about 70°-80° with the peduncle.
3. Overlapping petals, without touching, in the closed flower.

4. Slightly concave inside petals.

The accompanying color photographic drawings show the flower characteristics of Geneve, with colors being as true as possible with illustrations of this type.

Sheet 1 is a top perspective view of Geneve.

Sheet 2 is a closeup view showing in detail two blossoms of Geneve.

In the following description, color references are made to The Royal Horticultural Society Colour Chart (RHS) and to the Horticultural Color Chart (HCC).

Origin: Seedling.

Name: Geneve.

Class: Asiatic hybrids.

Parentage:

*Female parent.*—Mont Blanc.

*Male parent.*—Sterling Star.

Plant:

1. *Height (on opening of the anthers of the first flower)*:—Medium (5).
2. *Stalk.*—Anthocyanin coloring—present, weak, only at the base (9). Color: light green (1). Growth of Hair: present (9). Type of coat of hair: long (2). Division of coat of hair: especially in leaf axils — only distal (1). Internode length: uniform (2). Cross section: ribbed (3). Bulbils: lacking (1).
3. *Leaf.*—Position: spread out (2). Top angle of the base with the stalk: sharp, about 45°-50° (1). Length: medium (5). Width: medium (5). Thickness: normal (2). Form (middle third part of the stalk): narrow elliptic to thin oval (1). Color of the top: dark green (7). Luster of the top: weak (3). Growth of hair at the bottom: present (9). Division of the growth of hair on the bottom: only on distal part of stalk at utmost top of leaf. Top: pointed (2). Curve of the edge: lacking (1). Membraneous edge: lacking (1). Indentation of the edge: lacking (1). Uniformity: present (9). Form in cross section: angular (2). Top part: straight, to bending back (5). Flexibility: strong (1). Stalk: lacking (1).

Flower:

1. *Structure.*—Type: raceme (1). Growth of hair present: middle strong (9). Bracts: present (9). Number of bracts in comparison with the number of primary flowers: even (1). Bracteole: present (9). Number of bracteoles in comparison with the total number of flowers: equal (1). Position:

erect, to horizontal (3). Type: bowl-shaped, weak (3). Cross-section: large (7). Height of crown: medium (5). Length of longest flower stalk: medium (5).

2. *Petal.*—Length of longest exterior petal: medium (5). Width of widest exterior petal: medium (5). Length of longest interior petal: medium (5). Width of widest interior petal: medium (5). Color of the inside of the interior petal: near RHS 155D, but whiter; at the base, especially along the edges and in the center, diffuse reddish purple approaching HCC 25/3-625/3, which later disappears; edges of base have interrupted/-discontinuous dark purple line. Color of the outside of the interior petal: near RHS 155D, but whiter; along edges, with the exception of top, diffuse reddish purple, approaching HCC 26/3; middle nerve diffuse reddish purple, at the top greenish. Color of the inside of the exterior petal: near RHS 155D, color same as inside of interior petal but base is lighter with more diffuse reddish purple, near HCC 625/3; base edges lack line. Color of the outside of the exterior petal: near RHS 155D, but whiter, especially at base; median to top with diffuse reddish purple approaching HCC 25/3-625/3; top slightly thickened and green. Marking on the inside: present. (9). Color of the marking: dark purple. Type of marking on the inside: spots, (1) elliptic about $1\frac{1}{2} \times \frac{3}{4}$ mm. Density of the spots in the marking: thin. (3). Color of the inside of the throat: near RHS 155D, but whiter and more transparent. Color of the outside of the throat: near RHS 155D. Surface structure of the inside: ribbed and papillate, (4) honey gland about 19 mm long. Luster at the inside: lacking. (1). Curve of the edges of the petal: present, (9) very weak, only in exterior petals. Type of curve of the edge of the petals: rough. Flexure of petals: present. (9). Bended part of the petals: only top. (1). Extent of bending: weak. (3).

Reproductive organs:

*Length of stamina.*—Medium. (5)

*Color of the filaments.*—White. (1)

*Color of the anthers.*—Brown, (2) unripe.

*Color of the pollen.*—Light brown to light orange brown. (3)

*Length of the pistil.*—Short. (3)

*Color of the style.*—Light green, with slight hint of red. (2)

*Color of the stigma.*—Purple to diffuse reddish purple. (2)

Bulb:

*Type (in period of rest).*—Type 2.

*Top.*—Pointed. (1).

*Density of scales.*—Close. (7).

*Color of the exterior scales.*—White with a shade of yellow. (1).

*Top of the scales.*—Pointed. (1).

*Underground part of the stalk.*—bulbils — present. (9). roots — present. (9).

I claim:

1. A new and distinct cultivar of lily plant named Geneve, substantially as shown and described.

* * * * *

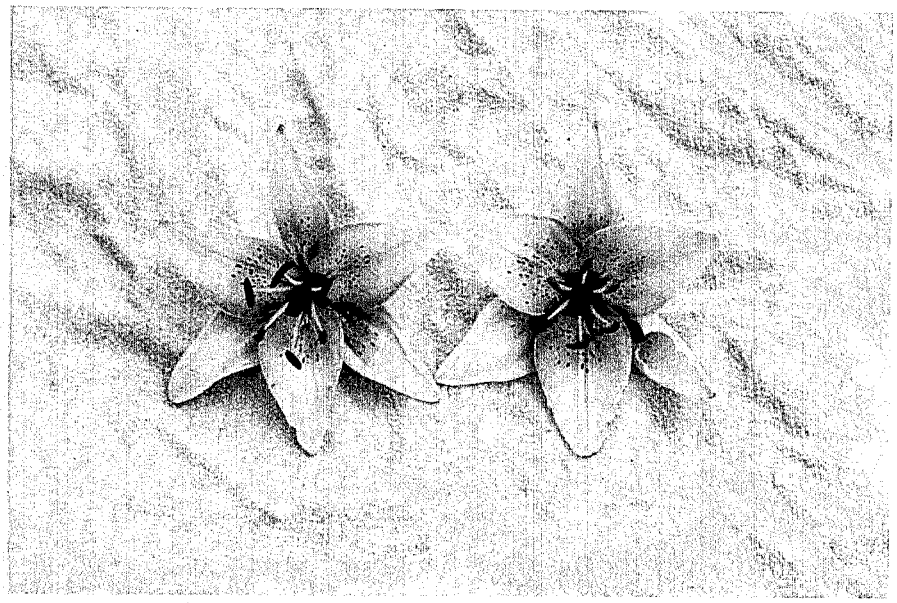

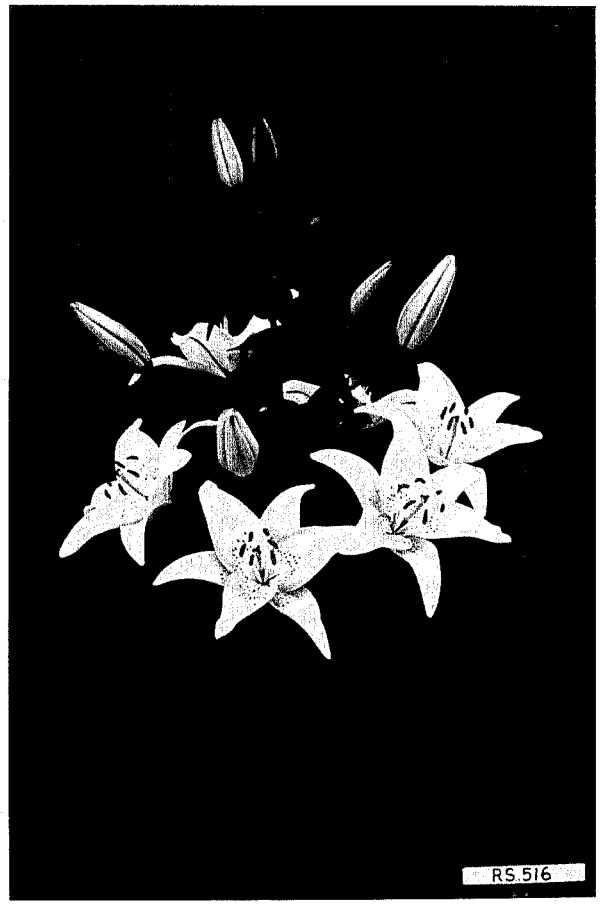
RS.516